United States Patent
Kramer et al.

(10) Patent No.: US 12,139,738 B2
(45) Date of Patent: Nov. 12, 2024

(54) PROCESSES AND SYSTEMS FOR BIOLOGICAL HYDROGEN PRODUCTION FROM ORGANIC WASTE USING YEAST

(71) Applicant: Purdue Research Foundation, West Lafayette, IN (US)

(72) Inventors: Robert A. Kramer, Crown Point, IN (US); Libbie S. W. Pelter, Schererville, IN (US); John A. Patterson, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 317 days.

(21) Appl. No.: 17/763,761

(22) PCT Filed: Sep. 25, 2020

(86) PCT No.: PCT/US2020/052812
§ 371 (c)(1),
(2) Date: Mar. 25, 2022

(87) PCT Pub. No.: WO2021/062218
PCT Pub. Date: Apr. 1, 2021

(65) Prior Publication Data
US 2022/0340937 A1    Oct. 27, 2022

Related U.S. Application Data

(60) Provisional application No. 62/906,261, filed on Sep. 26, 2019.

(51) Int. Cl.
*C12P 3/00* (2006.01)
*C12N 1/16* (2006.01)
*C12N 1/18* (2006.01)

(52) U.S. Cl.
CPC . *C12P 3/00* (2013.01); *C12N 1/18* (2013.01)

(58) Field of Classification Search
CPC ................ C12P 3/00; C12N 1/18; C12N 1/16
See application file for complete search history.

(56) References Cited

U.S. PATENT DOCUMENTS

| | | | |
|---|---|---|---|
| 10,246,724 B2 | 4/2019 | Kramer et al. | |
| 2010/0159539 A1 | 6/2010 | Ascon et al. | |
| 2011/0165639 A1 | 7/2011 | Ascon et al. | |
| 2014/0157777 A1* | 6/2014 | Kramer et al. | C12P 3/00 60/641.8 |

FOREIGN PATENT DOCUMENTS

| | | |
|---|---|---|
| WO | 2010085893 | 8/2010 |
| WO | 2013180756 | 12/2013 |

OTHER PUBLICATIONS

Battista F. et al.,., "Selection of the best pretreatment for hydrogen and bioethanol production from olive oil waste products", Renewable Energy, 2016, vol. 88, pp. 401-407. (Year: 2016).*
International Search Report and Written Opinion for International Patent Application No. PCT/US2020/052812, dated Jan. 29, 2021, 10 pages.

* cited by examiner

*Primary Examiner* — Satyendra K Singh
(74) *Attorney, Agent, or Firm* — Hartman Global IP Law; Gary M. Hartman; Domenica N. S. Hartman

(57) ABSTRACT

Processes and systems for biologically producing hydrogen gas from organic waste, including food waste. Such a process includes biologically producing hydrogen gas from organic waste by anaerobic fermentation of the organic waste with at least one strain of yeast.

10 Claims, 3 Drawing Sheets

PROCESSES AND SYSTEMS FOR BIOLOGICAL HYDROGEN PRODUCTION FROM ORGANIC WASTE USING YEAST

CROSS-REFERENCE TO RELATED APPLICATIONS

This application claims priority to International Patent Application No. PCT/US2020/052812 filed Sep. 25, 2020, which claims the benefit of U.S. Provisional Application No. 62/906,261, filed Sep. 26, 2019. The contents of these prior patent documents are incorporated herein by reference.

STATEMENT REGARDING FEDERALLY SPONSORED RESEARCH OR DEVELOPMENT

This invention was made with government support under Contract No. DE-FG36-06GO86050 awarded by the U.S. Department of Energy. The government has certain rights in the invention.

BACKGROUND OF THE INVENTION

The present invention generally relates to the biological production of hydrogen, and particularly relates to the biological production of hydrogen gas from organic waste using yeast.

Biological production of hydrogen gas offers a sustainable process for the production of fuel with a concurrent minimization of waste. Hydrogen gas has significant advantages as a clean energy source. Unlike fossil fuels, combustion of hydrogen does not produce carbon dioxide or oxides of nitrogen and sulfur. Hydrogen also has a higher energy yield (as an example, about 120 kJ/g) than hydrocarbons (as an example, about 44 kJ/g for petroleum). By using hydrogen in a fuel cell or a reciprocating engine, the major end products are electricity, water, and heat.

There are, however, technical and economic concerns with the production and storage of hydrogen impacting its near term viability. Conventional chemical processes for hydrogen production are energy intensive and therefore not cost effective. Biological hydrogen production processes offer a potentially economic and sustainable alternative for producing hydrogen. The use of microbial organisms is currently attracting increasing interest as a means of producing hydrogen, as indicated in multiple recent publications. Numerous studies have been conducted using microorganisms to generate hydrogen from fermentation of various substrates, nonlimiting examples of which are reported in Kapdan et al. Bio-hydrogen Production from Waste Materials, Enzyme Microbial Technology 38(5):569-582 (2006), and Chen et al., Using Sucrose as a Substrate in an Anaerobic Hydrogen-producing Reactor, Adv. Environ Res 7:695-699 (2003). Some studies have used a pure culture of bacteria, such as species of *Bacillus, Clostridium*, and *Enterobacter*, while others have used mixed cultures that originated from sludge, animal wastes, sewage, compost, soil, etc. Kummaravel et al., "Influence and Strategies for Enhanced Biohydrogen Production from Food Waste," Renewable and Sustainable Energy Reviews 92: 807-822 (2018), provides a survey of processes to produce hydrogen from food waste. Using organic wastes for bio-production of hydrogen not only has the potential to generate cost effective and renewable energy but also can reduce pollution in the environment.

BRIEF DESCRIPTION OF THE INVENTION

The present invention provides processes and systems for biologically producing hydrogen gas from organic waste, including food waste.

According to one aspect of the invention, a process includes biologically producing hydrogen gas from organic waste by anaerobic fermentation of the organic waste with at least one strain of yeast.

Technical aspects of processes and systems as described above preferably include the ability to use yeast, as opposed to bacteria, in a process that significantly increases hydrogen production as well as reduces processing and operating requirements, including minimal preprocessing of the organic waste and simplified operating conditions during hydrogen production.

Other aspects and advantages of this invention will be appreciated from the following detailed description.

BRIEF DESCRIPTION OF THE SEVERAL VIEWS OF THE DRAWING

In FIG. 2, hydrogen data are plotted in blue, and carbon dioxide data are plotted in green. In FIG. 3, hydrogen data are plotted in blue, carbon dioxide data are plotted in yellow, and overlapping hydrogen and carbon dioxide data appear as sienna.

DETAILED DESCRIPTION OF THE INVENTION

Figure 1:
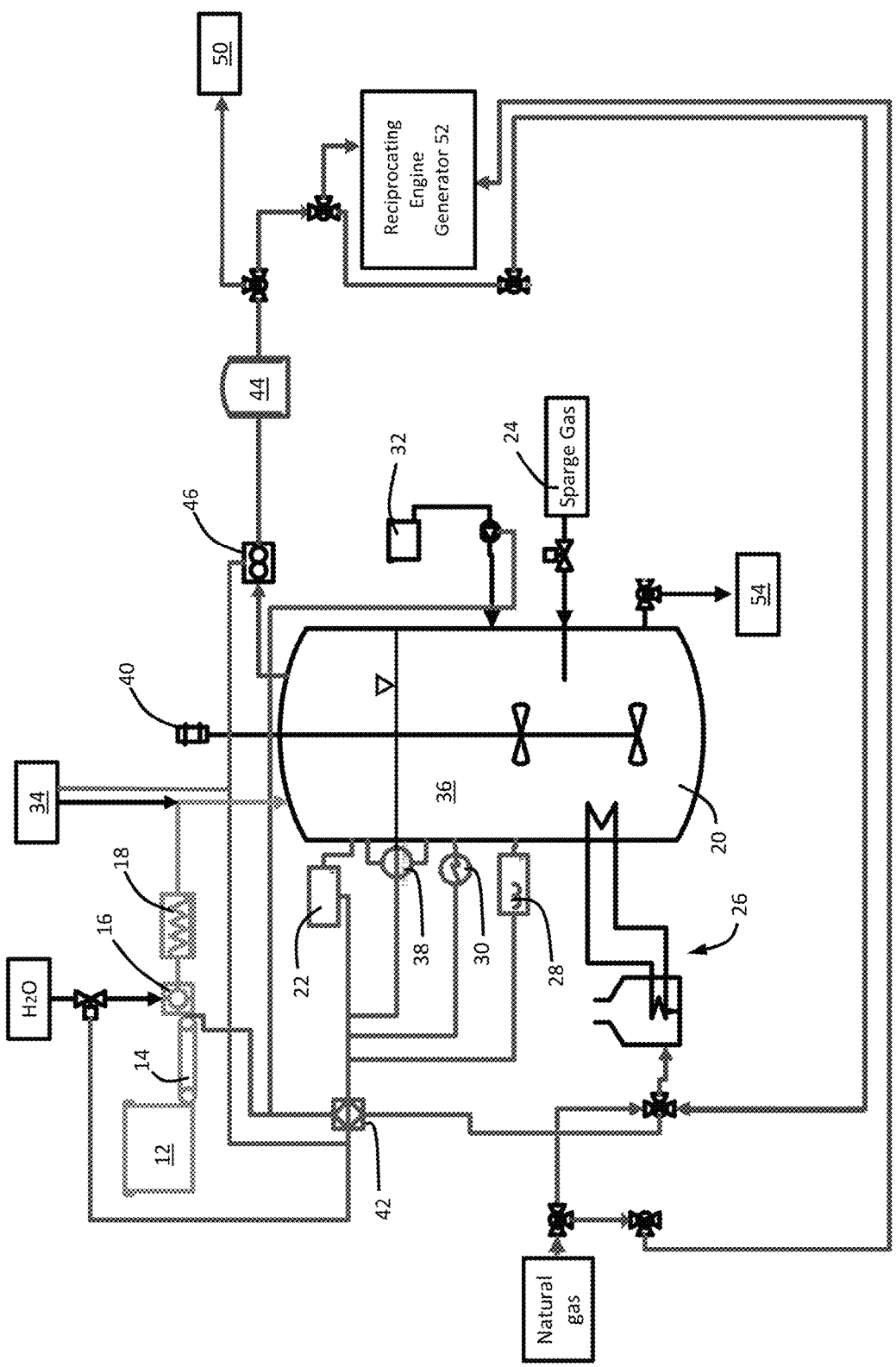
FIG. 1 schematically represents a system for biologically producing hydrogen gas from organic waste by anaerobic fermentation with at least one strain of yeast in accordance with a nonlimiting embodiment of this invention.

The following disclosure describes various aspects of processes and systems for biologically producing hydrogen gas from organic waste by anaerobic fermentation. A nonlimiting example of such a system is schematically represented in FIG. 1. The system represents an approach to producing hydrogen biologically from organic waste that employs yeast rather than bacteria to produce hydrogen from organic waste and increase hydrogen production relative to bacteria-based processes. Yeast particularly suitable for use in the system and process are those suitable for use in the commercial production of ethanol, as examples, *Saccharomyces cerevisiae* and species of the genus *Schizosaccharomyces*, although other strains of yeast also have shown hydrogen production capability. During investigations leading to the present invention, it was determined that the use of certain yeasts, as opposed to bacteria alone, has the ability to significantly increase productivity as well as reduce processing and operating requirements if the anaerobic fermentation process is performed within certain relatively narrow ranges of processing parameters. Minimal preprocessing is required for the organic waste and, aside from adhering to certain relatively narrow ranges of processing parameters, the operating conditions during hydrogen production are greatly simplified.

Generally, the nonlimiting embodiment of FIG. 1 represents organic waste (feedstock) as being delivered by a conveyor 14 from a receiving tank 12 to a grinder 16 where the waste is comminuted, and then fed to a reactor tank 20 with a screw pump 18. The reactor tank 20 is sealed and maintained at a low pressure, above atmospheric pressure but preferably not greater than about 0.25 psi (about 12 Pa) above atmospheric pressure. FIG. 1 further indicates that water (for example, tap water) is combined with the waste within the grinder 16. The pressure within the tank 20 is monitored with a pressure gauge 22 and controlled with a sparge gas 24 that is inert to the anaerobic fermentation process, for example, nitrogen. The temperature of the waste within the tank 20 is controlled, for example, by a heater 26 and thermostat 28, and the pH within the tank 20 is monitored with a pH meter 30 and controlled through the introduction of a base 32, as a nonlimiting example, a technical grade of sodium hydroxide (NaOH). Yeast 34 may be introduced directly into the tank 20 or, as shown, introduced into the tank 20 with the waste and water to form what is referred to herein as a mixture 36. The level of the mixture 36 within the tank 20 can be monitored with a level sensor 38. While within the tank 20, the mixture 36 is preferably agitated, for example, with a stirring apparatus 40. The system represented in FIG. 1 may be operated in either a batch or continuous mode. Outputs of the pressure gauge 22, thermostat 28, pH meter 30, and level sensor 38 and control of the heater 26 and introduction of the waste, water, sparge gas 24, base 32, and yeast 34 into the tank 20 are all fed to a suitable processor 42. Gaseous products (bio gas) 44 of anaerobic fermentation within the tank 20 are drawn from the tank 20 through a flow meter 46, which is also monitored with the processor 42. The gaseous products 44 are collected in a tank 48, from where the products 44 may be sold or utilized by downstream process applications 50, routed to a generator 52, or routed to the heater 26 as a fuel source. Residual waste 54 is drawn from the tank 20 for disposal.

In addition to hydrogen, carbon dioxide is a coproduct of the process performed by the system of FIG. 1. The gaseous product of the process may be about 50% hydrogen and about 50% carbon dioxide, which is a mixture that can be used to produce heat by direct combustion or to directly produce electricity in a reciprocating engine-driven generator, or produce electricity in a fuel cell after additional processing. While carbon dioxide is of concern as a greenhouse gas, carbon dioxide is much less of an environmental issue than methane ($CH_4$), which is internationally the most common product for organic waste digesters. If the source of the feedstock is food waste, the food crops that were the original source of the food waste may consume an equal or greater amount of carbon dioxide during normal growth than is released by the anaerobic fermentation of the food waste, in which case the process performed with the system of FIG. 1 is at least neutral from a carbon balance perspective.

Figure 2:
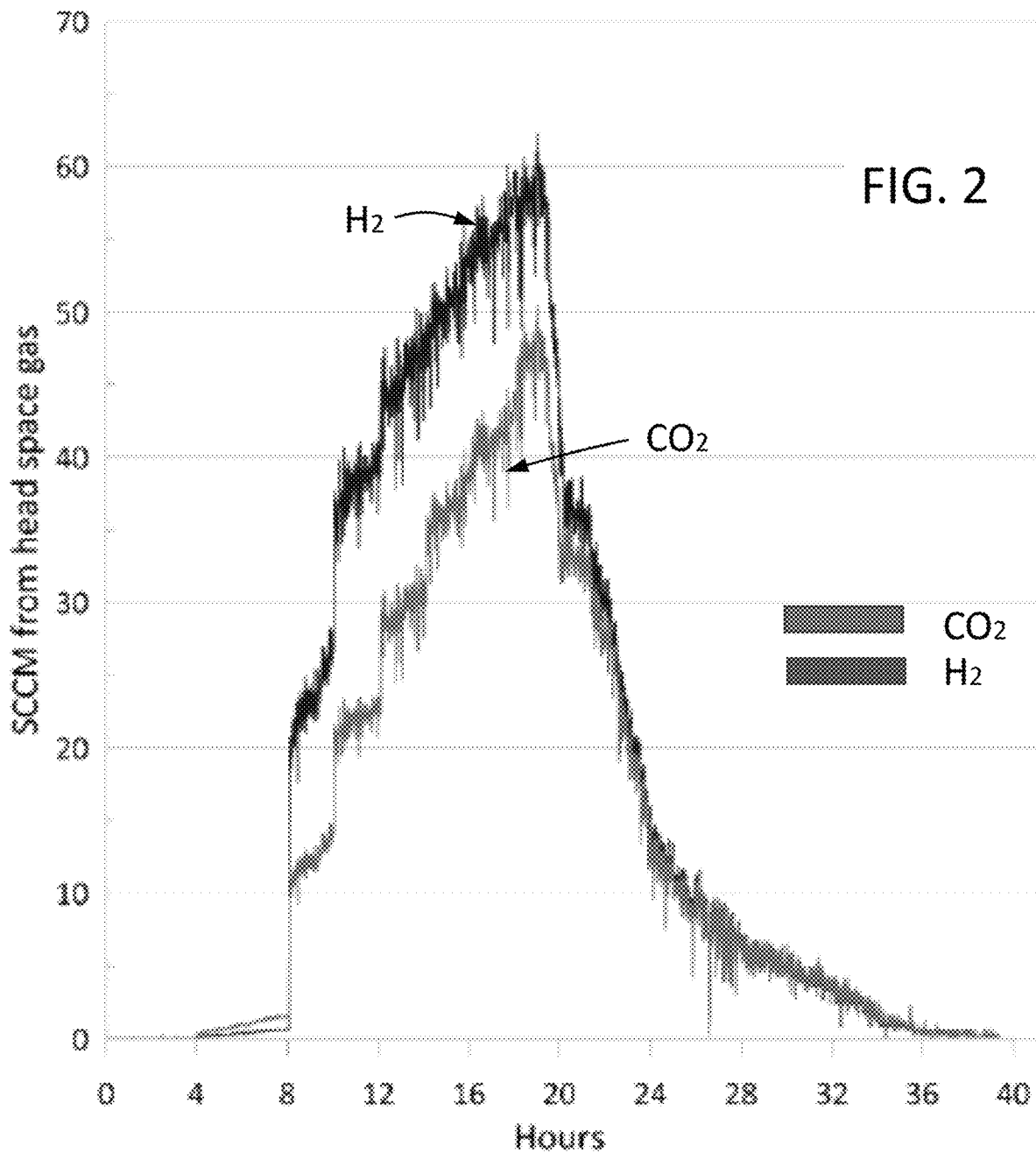
FIGS. 2 and 3 are graphs plotting gas production data obtained with systems of the type represented in FIG. 1.

Because yeasts used by the anaerobic fermentation process, as examples, *Saccharomyces cerevisiae* and species of the genus *Schizosaccharomyces*, are well known for use in winemaking, baking, brewing and ethanol production, notable aspects of the process performed with the system involve operating the system at specific conditions that will produce hydrogen as opposed to methane or ethanol. Optimal operating conditions were arrived at through testing of conditions that were developed through the use of multivariate analysis and statistical design of experiments. In a first investigation, about 200 g (dry equivalent) of food waste was combined with 7 liters of tap water in a 10-liter reaction tank. The tank had a head space above the wastewater mixture of about 2.75 liters. The food waste did not undergo any preprocessing other than grinding in a standard blender. In the tank, the waste-water mixture was combined with a commercial yeast used in ethanol production and agitated by stirring at about 130 RPM with a 4-cm diameter stirring paddle. The tank was maintained at a temperature of 37° C., at a pressure slightly above atmospheric pressure, and at a pH of 5.7 by means of a pump fed solution of 2M technical grade sodium hydroxide. Gas flow from the tank was measured with a mass flow meter. Gas composition was measure with a Micro Gas Chromatograph (CP-4900 Dual Channel Micro-GC; Varian Inc.). Pressure within the tank was continuously measured with a pressure transducer (Omega PX139) and recorded. The composition of the gaseous products drawn from the head space was determined and recorded every two hours with the Gas Chromatograph, and is plotted in FIG. 2.

The investigation evidenced that hydrogen can be biologically produced from organic waste using a process that employs yeast rather than bacteria as the basis for anaerobic fermentation. The majority of the hydrogen was produced within a 24-hour period. In contrast, processes for producing methane from organic waste can require weeks of fermentation time, and processes that produce hydrogen from organic waste using bacteria often require roughly double this time. As such, the investigation indicated that the process is capable of short production times to greatly increase productivity and value and allow for an associated reduction in production facility size. Complexity of a production facility implementing the system represented in FIG. 1 is also reduced because of the use of yeast instead of only bacteria.

In a second investigation, a food waste was synthesized with food materials described in Table 1.

TABLE 1

| Food Material | Mass (g) | Total Carbohydrate (mass %) | Total Fat (mass %) | Protein (mass %) | Fiber (mass %) |
|---|---|---|---|---|---|
| Dry Oatmeal | 575 | 67.5 | 7.5 | 12.5 | 10 |
| Bread | 614 | 45.6 | 2.6 | 8.8 | 3.5 |
| Mixed Vegetable | 472 | 13.3 | 0 | 2.2 | 3.3 |
| Carrot Juice | 935 | 6.8 | 0 | 0.9 | 0.4 |
| Raw Cabbage | 414 | 5.8 | 0 | 1.3 | 2.5 |

Figure 3:
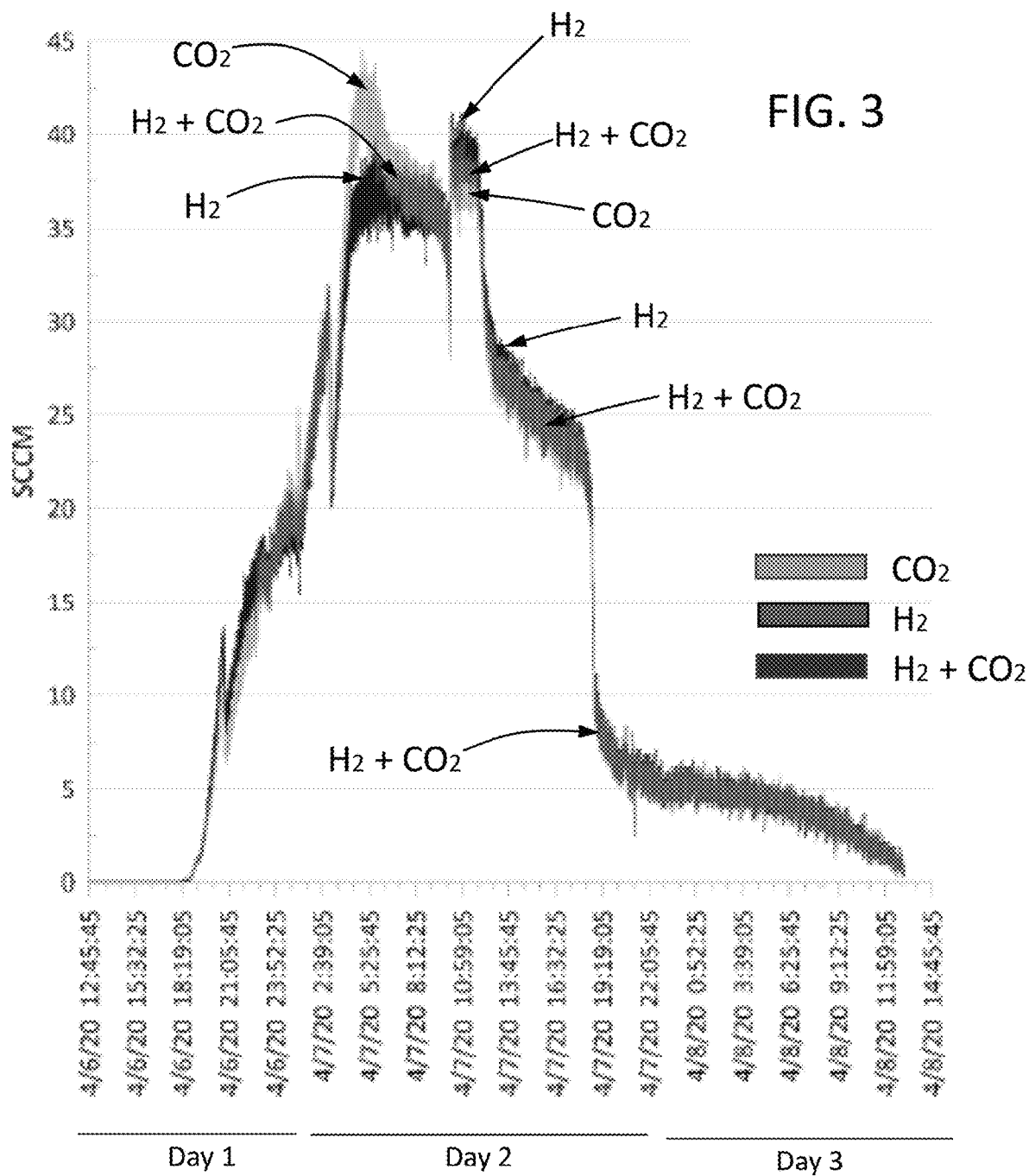

As with the first investigation, the food waste did not undergo any preprocessing other than grinding after being combined with water. In a 10-liter reactor tank, the waste-water mixture was combined with a commercial yeast used in ethanol production and agitated by stirring at about 120 RPM. The tank was maintained at a temperature of 37° C., at a near-atmospheric pressure of not greater than 0.25 psi (about 12 Pa) above atmosphere, and at a pH of 5.7 by means of a pump fed solution of technical grade sodium hydroxide. The production output of this process is plotted in FIG. 3, which shows a significant increase in hydrogen production compared to previous values. The data of FIG. 3 also evidence that hydrogen production rate using the system of FIG. 1 has been increased by a factor of approximately twelve over previous bacteria-based approaches bacteria (principally *Clostridium*). In addition, the time required for hydrogen production was decreased from 48 hours to less than 36 hours for the bulk of the gas production, and the concentration of hydrogen in the produced bio gas had increased from 25% for bacteria-based approaches to approximately 50% in the investigations reported above. Assuming the process scales up linearly, a 14,000-gallon (about 53,000-liter) reactor tank could produce approximately 360,000 liters of hydrogen at atmospheric pressure (STP) in about thirty-six hours.

Additional investigations have evidenced that the results reported above can be obtained if the process is carried out with certain relatively narrow ranges of processing parameters. The temperature range should be maintained in a range of about 32° C. to about 42° C. and the pH should be maintained in a range of about 5.5 to 5.9 pH to achieve appreciable hydrogen production. Agitation is also believed to be important, as is maintaining a positive pressure that is slightly above atmospheric pressure, preferably not greater than 0.25 psi (12 Pa) above atmospheric pressure. Yeast used in ethanol production performed better than yeasts conventionally used in brewing and standard bread yeasts. Because the process is anaerobic, an inert purge gas is employed as indicated in FIG. 1, and oxygen levels within the reactor tank are preferably less than 0.25%.

While the invention has been described in terms of particular embodiments and investigations, it should be apparent that alternatives could be adopted by one skilled in the art. For example, the process system and its components could differ in appearance and construction from the embodiments described herein and shown in the drawings, and functions of certain components of the process system could be performed by components of different construction but capable of a similar (though not necessarily equivalent) function, certain process parameters could be modified, and appropriate materials could be substituted for those noted. As such, it should be understood that the intent of the above detailed description is to describe the particular embodiments represented in the drawings and certain but not necessarily all features and aspects thereof, and to identify certain but not necessarily all alternatives to the particular embodiments represented in the drawings. As a nonlimiting example, the invention encompasses additional or alternative embodiments in which one or more features or aspects of the described embodiments could be eliminated. Accordingly, it should be understood that the invention is not necessarily limited to any particular embodiment represented in the drawings or described herein, and that the purpose of the above detailed description and the phraseology and terminology employed therein is to describe the particular embodiment represented in the drawings, as well as investigations relating to the particular embodiment, and not necessarily to serve as limitations to the scope of the invention. Therefore, the scope of the invention is to be limited only by the following claims.

The invention claimed is:

1. A process comprising biologically producing hydrogen gas from organic waste by anaerobic fermentation of the organic waste with at least one strain of yeast, wherein the anaerobic fermentation is performed in a reactor tank at an elevated temperature is about 32° C. to about 42° C., at a controlled pH of 5.5 to 5.9, at a pressure above atmospheric pressure but not greater than 12 Pa above atmospheric pressure, and at an oxygen level of less than 0.25% so that production of the hydrogen gas exceeds production of carbon dioxide over a period of twenty-four hours.

2. The process of claim 1, wherein water and the at least one strain of yeast are introduced to the reactor tank to form a mixture with the organic waste.

3. The process of claim 1, wherein the elevated temperature is about 37° C.

4. The process of claim 1, wherein the pH is 5.7.

5. The process of claim 1, wherein the pH is controlled with sodium hydroxide.

6. The process of claim 1, further comprising agitating the organic waste during the anaerobic fermentation.

7. The process of claim 1, wherein the anaerobic fermentation is performed on a mixture comprising the organic waste and water.

8. The process of claim 7, further comprising agitating the mixture during the anaerobic fermentation.

9. The process of claim 1, wherein the yeast is at least one of *Saccharomyces cerevisiae* and species of the genus *Schizosaccharomyces*.

10. The process of claim 1, wherein the organic waste is food waste.

* * * * *